(12) United States Patent
Cramb et al.

(10) Patent No.: US 10,935,778 B2
(45) Date of Patent: Mar. 2, 2021

(54) CONFOCAL MICROSCOPE WITH POSITIONABLE IMAGING HEAD

(71) Applicant: CALIBER IMAGING & DIAGNOSTICS, INC., Rochester, NY (US)

(72) Inventors: Allison L. Cramb, Rochester, NY (US); Christopher C. Distasio, Rochester, NY (US); William J. Fox, Rochester, NY (US); Steven Ridge, Glen Ellyn, IL (US); Simon C. Watkins, Pittsburgh, PA (US)

(73) Assignee: CALIBER IMAGING & DIAGNOSTICS, INC., Rochester, NY (US)

( * ) Notice: Subject to any disclaimer, the term of this patent is extended or adjusted under 35 U.S.C. 154(b) by 393 days.

(21) Appl. No.: 15/810,093

(22) Filed: Nov. 12, 2017

(65) Prior Publication Data
US 2018/0136448 A1    May 17, 2018

Related U.S. Application Data

(60) Provisional application No. 62/421,270, filed on Nov. 12, 2016.

(51) Int. Cl.
G02B 21/26    (2006.01)
A61B 5/00    (2006.01)
(Continued)

(52) U.S. Cl.
CPC ............ *G02B 21/26* (2013.01); *A61B 5/0059* (2013.01); *A61B 5/0068* (2013.01); *A61B 5/441* (2013.01);
(Continued)

(58) Field of Classification Search
CPC .................... G02B 21/26; G02B 21/0028; G02B 21/0032; G02B 21/0076; G02B 21/24;
(Continued)

(56) References Cited

U.S. PATENT DOCUMENTS 5,034,613 A    7/1991    Denk et al.
D354,761 S    1/1995    Komatsuzaki et al.
(Continued)

FOREIGN PATENT DOCUMENTS

CN    1349122 A    5/2002
DE    19835070 A1    2/2000
(Continued)

OTHER PUBLICATIONS

Stereo Microscope Boom Stands, Diagnostic Instruments, Inc., Catalog #BS-3, 2003.
(Continued)

*Primary Examiner* — Stephone B Allen
*Assistant Examiner* — Adam W Booher
(74) *Attorney, Agent, or Firm* — Kenneth J. LuKacher Law Group; Kenneth J. LuKacher

(57) ABSTRACT

A confocal microscope for imaging tissue having an imaging head for capturing optically formed microscopic sectional images of tissue samples, a platform upon which is disposed a linear stage for moving the imaging head along a vertical dimension, and a rotary stage to rotate the linear stage and imaging head about the vertical dimension. A mounting arm couples the imaging head to the linear stage to adjust tilt of the imaging head and to rotate the imaging head about a normal axis perpendicular to an optical axis of an objective lens of the imaging head. In a first mode of operation, the imaging head is positioned to image an ex-vivo or in-vivo tissue sample upon the platform, such as ex-vivo tissue sample mounted upon a movable specimen stage, and in a
(Continued)

second mode of operation the imaging head is positioned to image an in-vivo tissue sample beside the platform.

20 Claims, 11 Drawing Sheets

(51) Int. Cl.
    *G02B 21/00*     (2006.01)
    *A61B 90/20*     (2016.01)
    *G02B 21/24*     (2006.01)
    *G02B 21/36*     (2006.01)

(52) U.S. Cl.
    CPC ............ *A61B 5/7225* (2013.01); *A61B 90/20* (2016.02); *G02B 21/0028* (2013.01); *G02B 21/0032* (2013.01); *G02B 21/0076* (2013.01); *G02B 21/24* (2013.01); *G02B 21/248* (2013.01); *G02B 21/361* (2013.01); *G02B 21/368* (2013.01); *A61B 2562/0233* (2013.01)

(58) Field of Classification Search
    CPC .. G02B 21/248; G02B 21/361; G02B 21/368; G02B 21/0024; G02B 21/36; G02B 21/362; A61B 90/20; A61B 90/25; A61B 5/0059; A61B 5/0068; A61B 5/441; A61B 5/7225; A61B 5/0062; A61B 2562/0233
    See application file for complete search history.

(56) References Cited

U.S. PATENT DOCUMENTS

| | | | |
|---|---|---|---|
| 5,532,874 | A | 7/1996 | Stein |
| 5,788,639 | A | 8/1998 | Zavislan et al. |
| 5,820,623 | A | 10/1998 | Ng |
| 5,861,983 | A | 1/1999 | Twisselman |
| 5,880,880 | A | 3/1999 | Anderson et al. |
| 5,982,532 | A | 11/1999 | Mittelstadt et al. |
| 6,137,628 | A | 10/2000 | Kraft et al. |
| 6,167,173 | A | 12/2000 | Schoeppe et al. |
| 6,330,106 | B1 | 12/2001 | Greenwald et al. |
| 6,411,434 | B1 | 6/2002 | Eastman et al. |
| 6,434,416 | B1 | 8/2002 | Mizoguchi et al. |
| D492,997 | S | 7/2004 | Distasio |
| D523,883 | S | 6/2006 | Distasio et al. |
| 7,227,630 | B1 | 6/2007 | Zavislan et al. |
| 7,394,592 | B2 | 7/2008 | Fox et al. |
| 7,564,625 | B2 | 7/2009 | McLeod et al. |
| 7,864,996 | B2 | 1/2011 | Hemmer et al. |
| D690,342 | S | 9/2013 | Funakoshi et al. |
| 8,759,745 | B2 | 6/2014 | Klose et al. |
| 9,055,867 | B2 | 6/2015 | Fox et al. |
| 9,229,210 | B2 | 1/2016 | Fox et al. |
| D771,169 | S | 11/2016 | Weber |
| D784,433 | S | 4/2017 | Weber |
| D812,665 | S | 3/2018 | Klein et al. |
| 10,514,532 | B1 | 12/2019 | Cramb et al. |
| 2002/0097486 | A1* | 7/2002 | Yamaguchi .......... G02B 21/248 359/380 |
| 2003/0206341 | A1 | 11/2003 | Wolleschensky et al. |
| 2003/0218746 | A1* | 11/2003 | Sampas .............. G01N 21/6428 356/318 |
| 2004/0133112 | A1 | 7/2004 | Rajadhyaksha |
| 2005/0213201 | A1 | 9/2005 | Zimmermann et al. |
| 2007/0160279 | A1 | 7/2007 | Demos |
| 2007/0236786 | A1 | 10/2007 | McLeod et al. |
| 2007/0285813 | A1 | 12/2007 | Lasser et al. |
| 2008/0151368 | A1 | 6/2008 | Weiss |
| 2010/0207036 | A1 | 8/2010 | Massonneau et al. |
| 2012/0162602 | A1 | 6/2012 | Huening et al. |
| 2013/0324846 | A1* | 12/2013 | Yaroslavsky ........ A61B 5/0071 600/431 |
| 2014/0009596 | A1* | 1/2014 | Bresolin ............... G06T 7/0012 348/79 |
| 2016/0231552 | A1 | 8/2016 | Hein |
| 2016/0313252 | A1* | 10/2016 | Rachet ............... G01N 33/4833 |
| 2017/0227753 | A1* | 8/2017 | Kamata .................. A61B 90/20 |

FOREIGN PATENT DOCUMENTS

| | | | |
|---|---|---|---|
| DE | 102005020542 A1 | 11/2006 | |
| EP | 0293228 | 11/1988 | |
| WO | WO-2006078956 A2 * | 7/2006 | ............. G02B 21/26 |
| WO | WO-2014085911 A1 * | 6/2014 | ......... G01B 9/02091 |

OTHER PUBLICATIONS

Dual Linear Ball Bearing Arm, Old School Industries, Inc., http://www.osi-incorp.com/productdisplay/dual-linear-ball-earing-arm, printed Sep. 25, 2015.
Office Action dated Jun. 13, 2018 with Notice of References Cited for U.S. Appl. No. 15/277,380, filed Sep. 27, 2016.
Office Action dated Jan. 23, 2019 with Notice of References Cited for U.S. Appl. No. 15/277,380, filed Sep. 27, 2016.
VivaScope(R) 1500/3000, MAVIG GmbH, 2011.
U.S. Appl. No. 15/277,380, filed Sep. 27, 2016 with Filing Receipt.
Scanning Stage SCANplus IM, Marzhauser Wetzlar Gmbh & Co. KG, Mar. 2016.
Velmex Rotary Tables, Velmex, Inc., at least as early as Nov. 6, 2016.
Motorized BiSlide Systems, Velmex, Inc., http://www.velmex.com/Products/BiSlide/BiSlide_Motorized.html, printed Nov. 6, 2016.
Precision Rotation Stage Model UTR80, Newport Corp., http://www.newport.com/p/UTR80, printed Nov. 7, 2016.
Vexta 2-Phase Stepping Motor, http://www.skycraftsurplus.com/vexta2-phasesteppingmotor18degstep.aspx, printed Nov. 9, 2016.
Rajadhyaksha, Milind et al., Confocal Laser Microscope Images Tissue in vivo, Laser Focus World, pp. 119-127, Feb. 1997.
Schmitt et al., Optical Characterization of Disease Tissues Using Low-coherence Interferometry, Proc. of SPIE, vol. 1889, pp. 197-211, 1993.
VivaScope(R), MAVIG GmbH, 2011.
VivaScope(R) 2500 Multilaser, MAVIG GmbH, 2010.
Rajadhyaksha, Milind et al., "In vivo Confocal Scanning Laser Microscopy of Human Skin: Melanin Provides Strong Contrast," The Journal of Investigative Dermatology, vol. 104, No. 6, pp. 946-952, Jun. 1995.
European Patent Application No. 17 868 634.1, Extended European Search Report, and Opinion, dated Oct. 9, 2020.
European Patent Application No. 17 868 634.1, Supplementary Partial European Search Report, and Provisional Opinion, dated Jul. 7, 2020.

* cited by examiner

CONFOCAL MICROSCOPE WITH POSITIONABLE IMAGING HEAD

This application claims priority to U.S. Provisional Patent Application No. 62/421,270, filed Nov. 12, 2016, which is incorporated herein by reference.

FIELD OF THE INVENTION

The present invention relates to a confocal microscope having a positionable imaging head mounted to a platform, and particularly to, a confocal microscope having an imaging head mounted to a platform positionable in one mode to image tissue samples disposed upon the platform, such as an ex-vivo tissue specimen on a movable specimen stage, and in another mode to image tissue samples beside the platform, such as in-vivo skin tissue of large animals or humans.

BACKGROUND OF THE INVENTION

Confocal microscopes optically section tissue to produce microscopic images of tissue sections without requiring histological preparation of the tissue on slides (i.e., slicing, slide mounting, and staining). Such sectional images produced may be on or under the surface of the tissue. An example of a confocal microscope is the VivaScope® manufactured by Caliber Imaging & Diagnostics, Inc. of Henrietta, New York. Examples of confocal microscopes are described in U.S. Pat. Nos. 5,788,639, 5,880,880, 7,394,592, and 9,055,867. In particular, U.S. Pat. No. 7,394,592 describes an imaging head of a confocal microscope mounted on a multi-positionable arm extending from an upright station having a computer system connected to the imaging head, where the computer system shows on a display confocal images captured by the microscope. While useful for imaging in-vivo tissue, such as a skin lesion without removal from a patient, it is cumbersome when one wishes to image ex-vivo tissue samples as may be mounted on a microscope stage. Other confocal microscopes have been developed for use in imaging ex-vivo tissue samples, such as may be mounted in tissue cassette holders, as described in U.S. Pat. Nos. 6,411,434, 6,330,106, 7,227,630, and 9,229,210. It would be desirable to provide a confocal microscope from a common platform which can be used both for imaging ex-vivo tissue samples mountable upon a stage and in-vivo tissue samples of a patient or animal.

SUMMARY OF THE INVENTION

Accordingly, it is an object of the present invention to provide a confocal microscope having an imaging head supported from a platform where the imaging head is positionable over the platform or beside the platform as desired for imaging tissue samples, thereby enabling ex-vivo imaging of tissue samples as may be disposed on a stage upon the platform and in-vivo imaging of tissue samples as may be disposed beside the platform.

Briefly described, the present invention embodies a microscope for imaging tissue having an imaging head with an optical system for capturing optically formed microscopic sectional images, and a platform upon which is disposed first and second stages. The first stage is coupled to the imaging head for moving the imaging head along a vertical dimension perpendicular to a horizontal dimension along which the platform extends, such as to adjust a height of the imaging head. The second stage rotates the imaging head about the vertical dimension. The imaging head is positionable using at least the first and second stages in a first mode to image at least a first tissue sample disposed between the imaging head and the platform (i.e., upon the platform), and in the second mode to image at least a second tissue sample disposed beside the platform (i.e., not upon the platform). Preferably, the optical system is operative by confocal microscopy, such that the microscope of the present invention is referred to as a confocal microscope, but other modalities for capturing optically formed microscopic sectional images may be used.

In the first mode of the microscope operation, the first tissue sample may be an ex-vivo tissue specimen (e.g., excised from a patient/subject) or in-vivo tissue of small animal or subject disposed upon the platform. While in the second mode of microscope operation, the second tissue sample may be in-vivo skin tissue of a human or large animal subject.

The optical system of the imaging head comprises optics having at least an objective lens for focusing and collecting illumination from the first and second tissue samples when each face the objective lens. The second stage is preferably a rotary stage between the first stage and the platform for rotating the first stage and the imaging head coupled thereto 360 degrees about the vertical dimension. The first stage may be a linear slide stage having a carriage movable along the vertical dimension, in which such carriage is coupled to the imaging head by a mounting arm. The mounting arm has a first portion fixed to the carriage, and a second portion having a rotary stage for rotating the imaging head about a normal axis perpendicular to the optical axis of the objective lens. The second portion is further tiltable with respect to the first portion to adjust tilt of the imaging head along the normal axis with respect to the horizontal dimension. The rotary stage and tilt adjustment provided by the mounting arm, and the first and second stages, provides the imaging head with multiple (four) degrees of freedom of motion so it can be set by a user to different positions to image ex-vivo or in-vivo tissue samples from a common platform upon which the imaging head is mounted in either first or second modes.

A third stage, such as an x-y stage, may be mounted to the platform movable along x and y orthogonal axes along the horizontal dimension along which the platform extends. The first tissue sample, such as ex-vivo tissue, is mounted upon such third stage for moving the tissue sample with respect to the objective lens during first mode operation of the microscope. The optical axis of the objective lens is aligned to extend along a z axis perpendicular to the x and y axes. This may be achieved by one or more of the above described rotation about the normal axis and tilt of the imaging head until the optical axis aligns along the z axis. An optional fourth stage may be mounted to the third stage moveable along such z axis, where the first tissue sample is mounted instead upon the fourth stage to enable the tissue sample to be movable using the third and fourth stages along x, y, and z axes with respect to the objective lens. While the objective lens is movable within the imaging head along its optical axis, the fourth stage can provide additional control for positioning the tissue sample along the z axis. The microscope may further be used in the first mode with the third and fourth stages removed from the platform, if desired. The third stage (and fourth stage if mounted thereto) may be referred to herein as a specimen stage.

The microscope has a computer system connected to the imaging head to receive signals representative of the images of the first or second tissue samples when imaged. The computer system shows on a display and/or store in its memory the images captured by the microscope. The computer system controls operation of the imaging head responsive to a user via user interface device(s) provided. Movement of x and y axis motors of the third stage, and z axis motor of the fourth stage (if present), are also preferably controlled by the computer system, but may alternatively be controlled by a joystick if provided.

The optical system in the imaging head can utilize multiple discrete laser wavelengths for illumination, and selectable wavelengths for detection. However, a single wavelength of laser illumination and detection may be used. The objective lens may be removably mounted to the microscope, such as by magnetics, so that different objective lens may be mounted thereto, as desired by a user.

In the preferred embodiment, the objective lens of the optical system focuses and collects scanned illumination from a tissue sample, where the scanned illumination travels along a first path via the objective lens to the tissue sample, and collected return illumination travels along a second path via the objective lens. The second path has at least a beam splitter that splits the return illumination into first and second beams. The first beam travels to a first detector via a first pinhole and a first selected position of an optical filter or opening (such along of a first filter wheel), and the second beam travels to a second detector via a second pinhole and a second selected position of another optical filter or an opening (such along of a second filter wheel). One or both of the first pinhole and second pinhole are each separately adjustable in position to align their first and second beams, respectively, onto their first detector and second detector, respectively.

The optical system may further have a mirror in the second path to reflect the return illumination onto the beam splitter. Such mirror may be adjustable in position to align the first beam when split by the beam splitter onto the first detector via the first pinhole, which may then be non-adjustable in position, and the second pinhole is adjustable in position to align the second beam via the second pinhole onto the second detector. Alternatively, the mirror may be non-adjustable in position, and one (or preferably) both the first and second pinholes are each separately adjusted in position to align their respective first and second beams onto their respective first and second detectors.

As the illumination of the tissue sample is of multiple discrete wavelengths, the first and second detectors receive different wavelengths of the collected illumination to enable simultaneous capture of a same one of the images at the different wavelengths or wavelength range on the first and second detectors in accordance with the first selected position and the second selected position having at least one of the optical filter and the another optical filter, respectively. Where one or more of the discrete wavelengths of illumination can activate fluorescent dye(s) that may be applied to tissue sample, the optical filter in the path of one of the first or second beams is selected to enable detection of fluorescent wavelength(s) associated with the dye(s) on their associated detector. Where non-fluorescent imaging is desired, an open position is selected in the path of one of the first or second beams to detect light of a discrete wavelength of illumination that was present along the first path to the tissue sample.

BRIEF DESCRIPTION OF THE DRAWINGS

The foregoing objects, features, and advantages of the invention will become more apparent from a reading of the following description in connection with the accompanying drawings, in which:

FIG. 1 shows an example of an ex-vivo tissue sample being imaged and FIG. 2 shows an example of an in-vivo tissue sample being imaged;

DETAILED DESCRIPTION ON THE INVENTION

Figure 1:
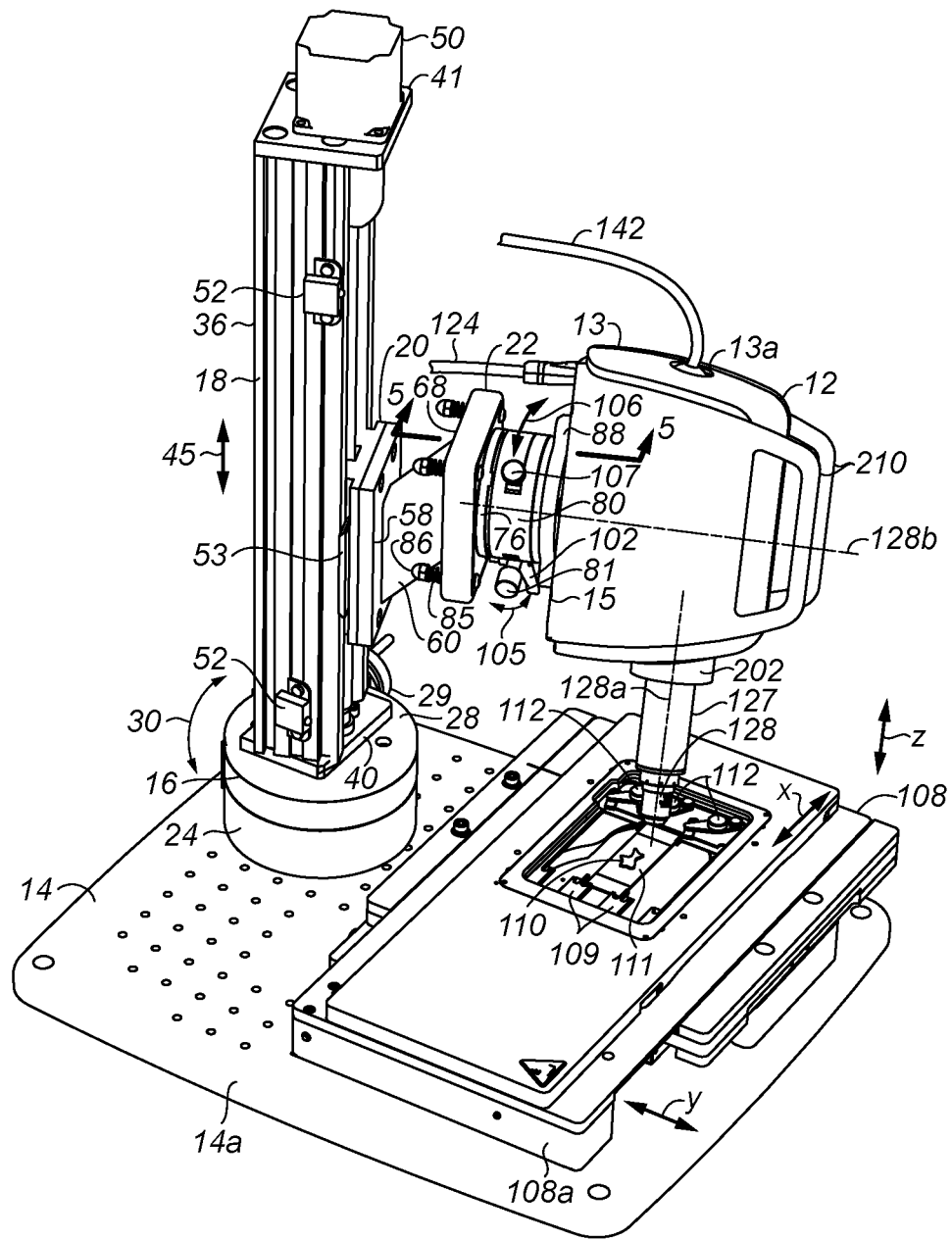
FIGS. 1 and 2 are two perspective views taken from different angles of the imaging head of the microscope of the present invention mounted to a platform, where
Figure 2:
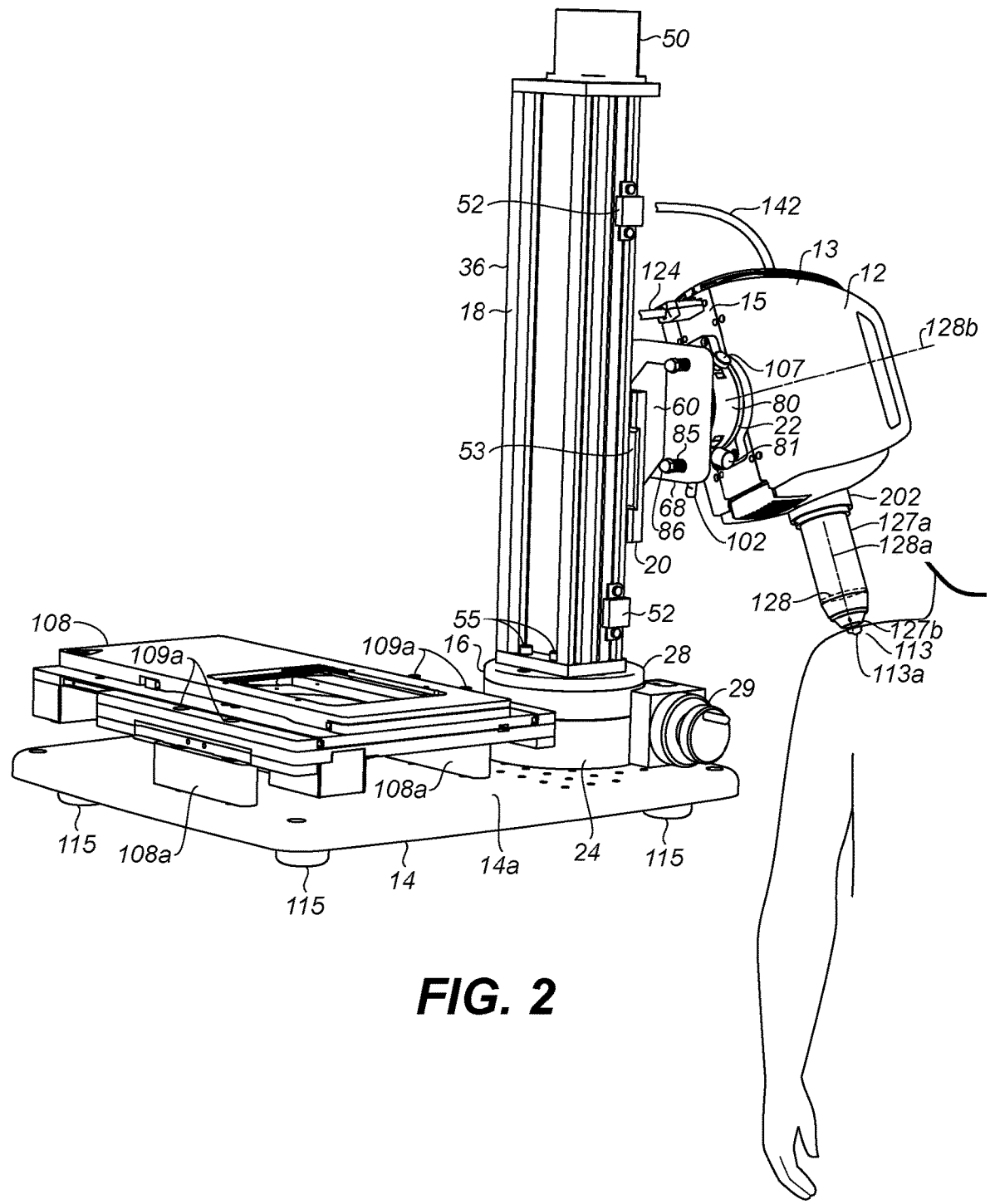
Figure 3:
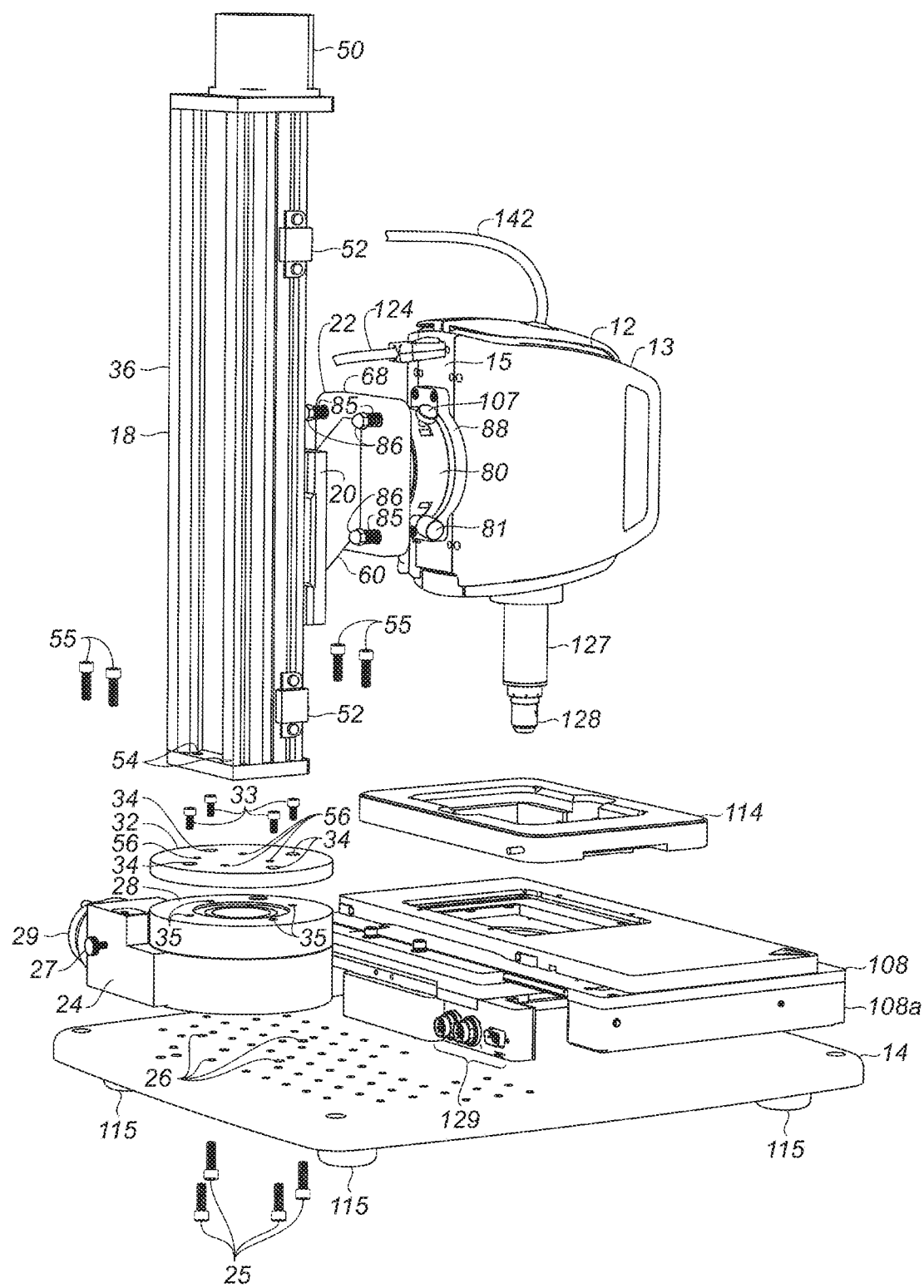
FIG. 3 is another view of the imaging head of FIG. 1 and the platform in which the assembly of a rotary stage and a vertical stage are shown exploded from the platform, and an x-y stage is shown with an exploded optional z-stage mountable upon the x-y stage.

Referring to FIGS. 1, 2, and 3, an imaging head 12 of a microscope 10 (FIG. 8) is shown in a housing 13 supported over a platform (or base) 14 having an upper surface 14a along a horizontal or dimension or plane. A second (or rotary) stage 16 is mounted to platform 14 for rotating a first (or vertical) stage 18 about a vertical dimension, i.e., perpendicular to the horizontal dimension along which upper surface 14a of platform 14 extends. Vertical stage 18 is a vertically disposed linear slide stage which carries a movable carriage 20 for translation along such vertical dimension. Carriage 20 is coupled by a mounting arm 22 to a base 15 of housing 13 of imaging head 12. The mounting arm 22 enables adjustment of tilt and rotation of the imaging head 12 at a desired adjustable rotational position and height position as set by rotary stage 16 and vertical stage 18, respectively, as will be described later below in more detail.

Figure 9:
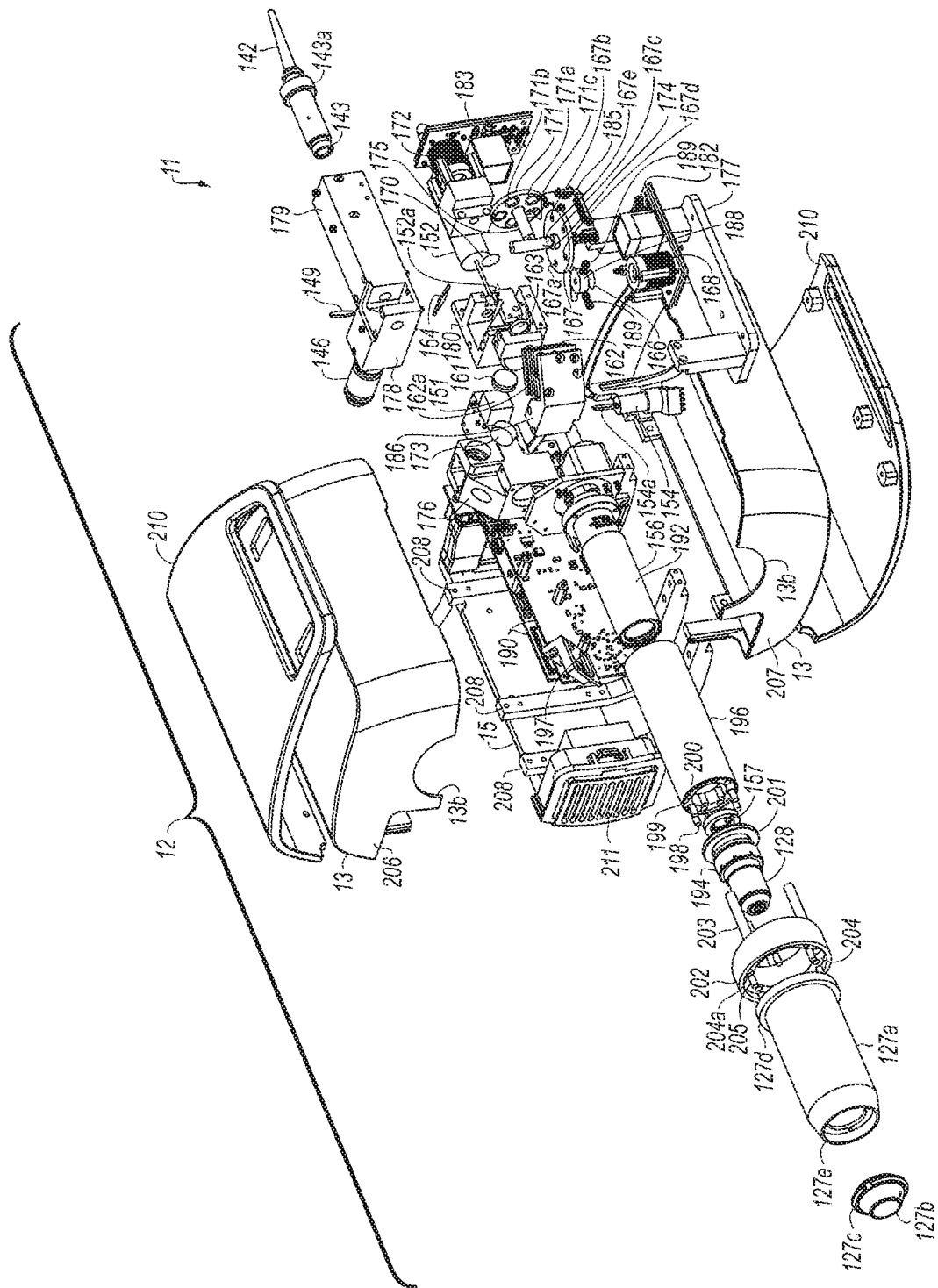
FIG. 9 is an exploded perspective view of the imaging head of FIG. 1 apart from the rest of the microscope of FIG. 8.
Figure 10:
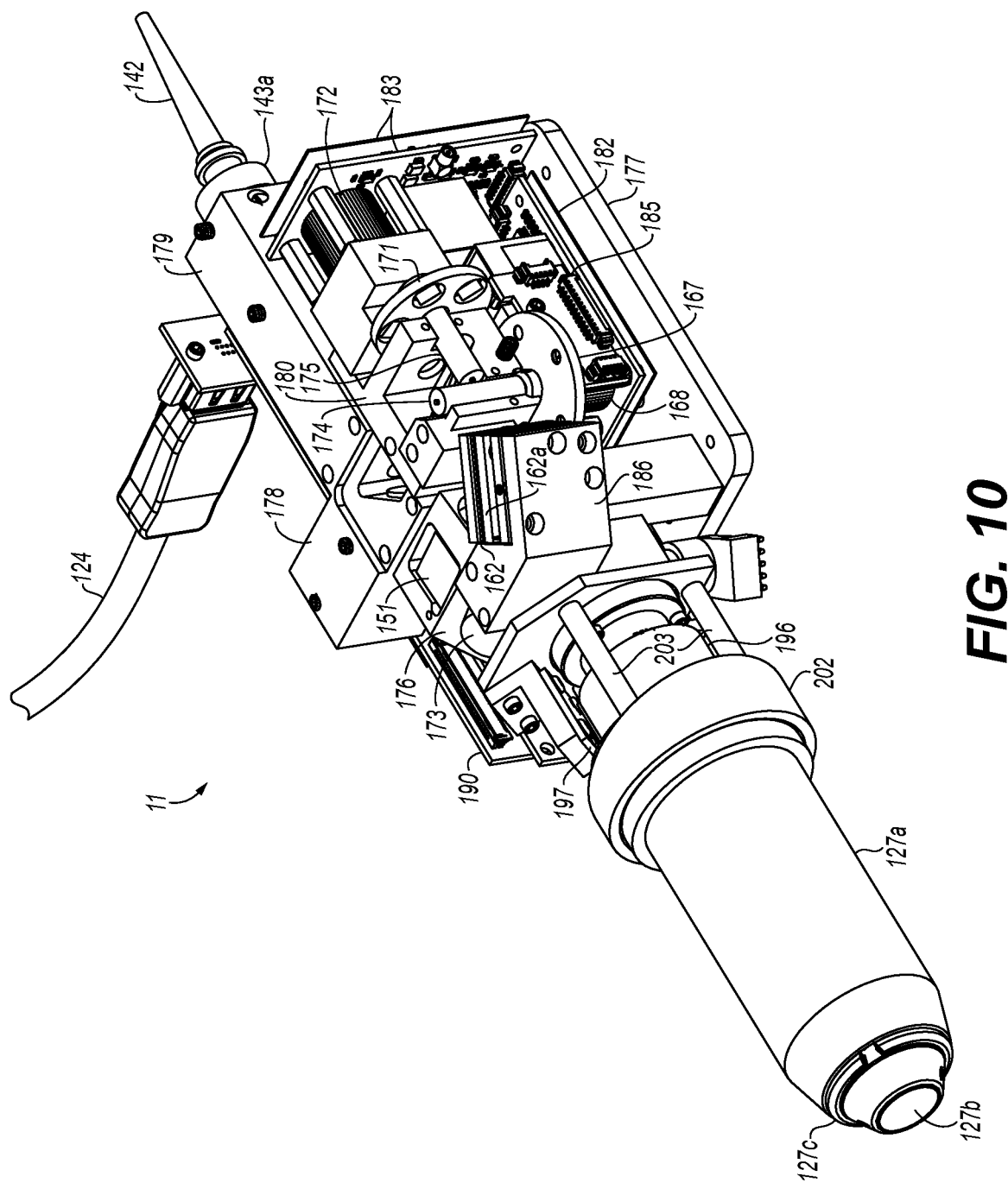
FIG. 10 shows the imaging head of FIG. 9 assembled with the housing of the imaging head removed.
Figure 11:
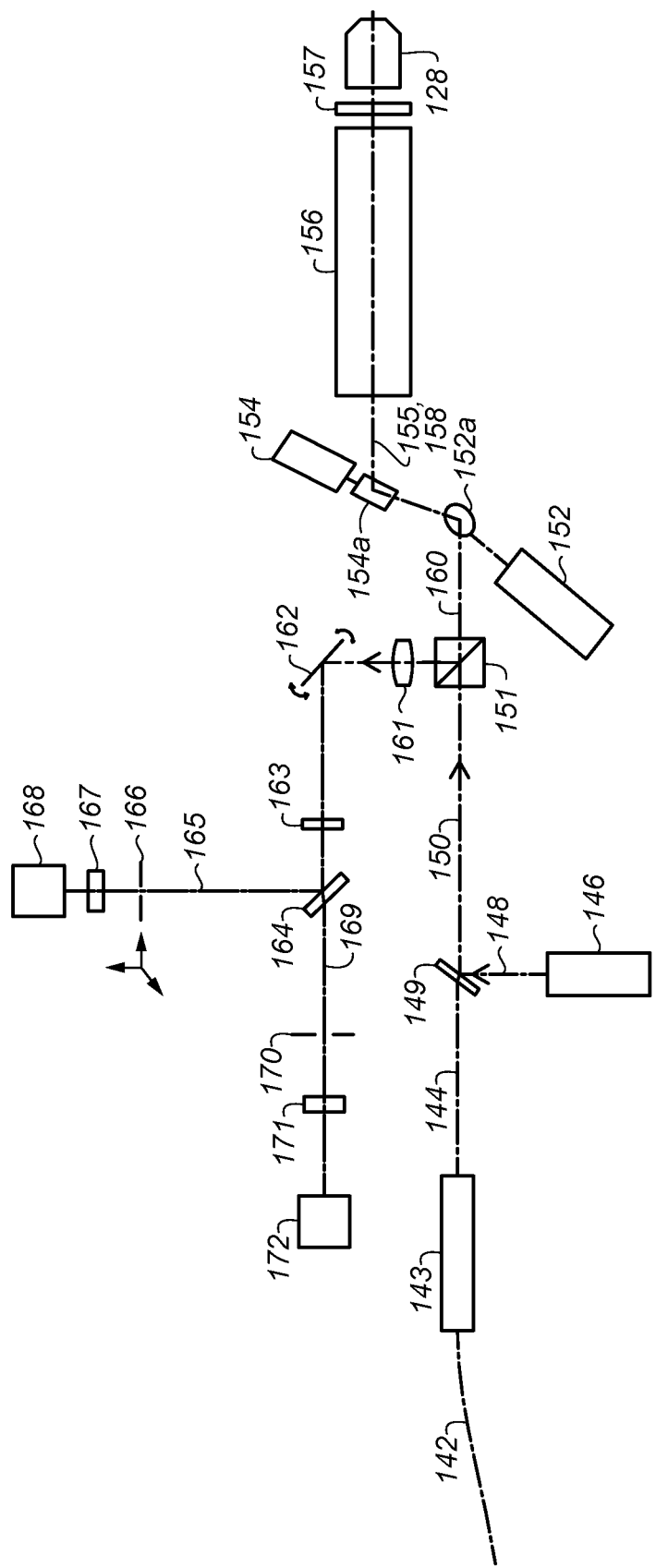
FIG. 11 is an optical diagram of the optical system in the imaging head of FIG. 1.

The imaging head 12 has an optical system 11 for capturing optically formed microscopic sectional images of tissue samples. The operation and structure of imaging head 12 may be the same as the confocal microscope of U.S. Pat. No. 9,055,867 which is incorporated herein by reference, but the preferred optical system 11 is shown in FIGS. 9-11. The optical system 11 has an objective lens 128 within an extending snout 127 of the imaging head 12 for focusing and collecting illumination from tissue samples facing the objective lens. Objective lens 128 has an optical axis 128a, and perpendicular to such optical axis 128a is a virtual normal axis 128b. Axes 128a and 128b are depicted as dashed lines in FIGS. 1 and 2.

Rotary stage 16 has a base 24, which is mounted to platform 14 by screws 25 via threaded holes 26 (FIG. 3) in platform 14, and a turntable 28 which rotates with respect to base 24, as indicated by arrow 30, responsive to rotation of a graduated knob (or hand crank) 29 to gearing (not shown) disposed to rotate turntable 28. A locking pin 27 may slide or be turned to move in and out with respect to a hole in base 24 in order to lock and unlock, respectively, the rotational position of turntable 28 with respect to base 24. Turntable 28 is rotatable 360 degrees and may have graduations along its outer circumference in rotational degrees with respect to marking(s) along base 24, which may be utilized by a user when manually turning knob 29 clockwise or counterclockwise to effect desired rotation. The rotary stage 16 is preferably a Velmex rotary table, model no. A4872TS (manufacturer: Velmex, Inc., Bloomfield, N.Y. USA), but other rotary tables may also be used. A circular adapter plate 32 is mounted atop turntable 28 by screws 33 received in threaded holes 34 of the adapter plate 32 and threaded holes 35 of turntable 28. Adapter plate 32 may be made of stainless steel.

Figure 4:
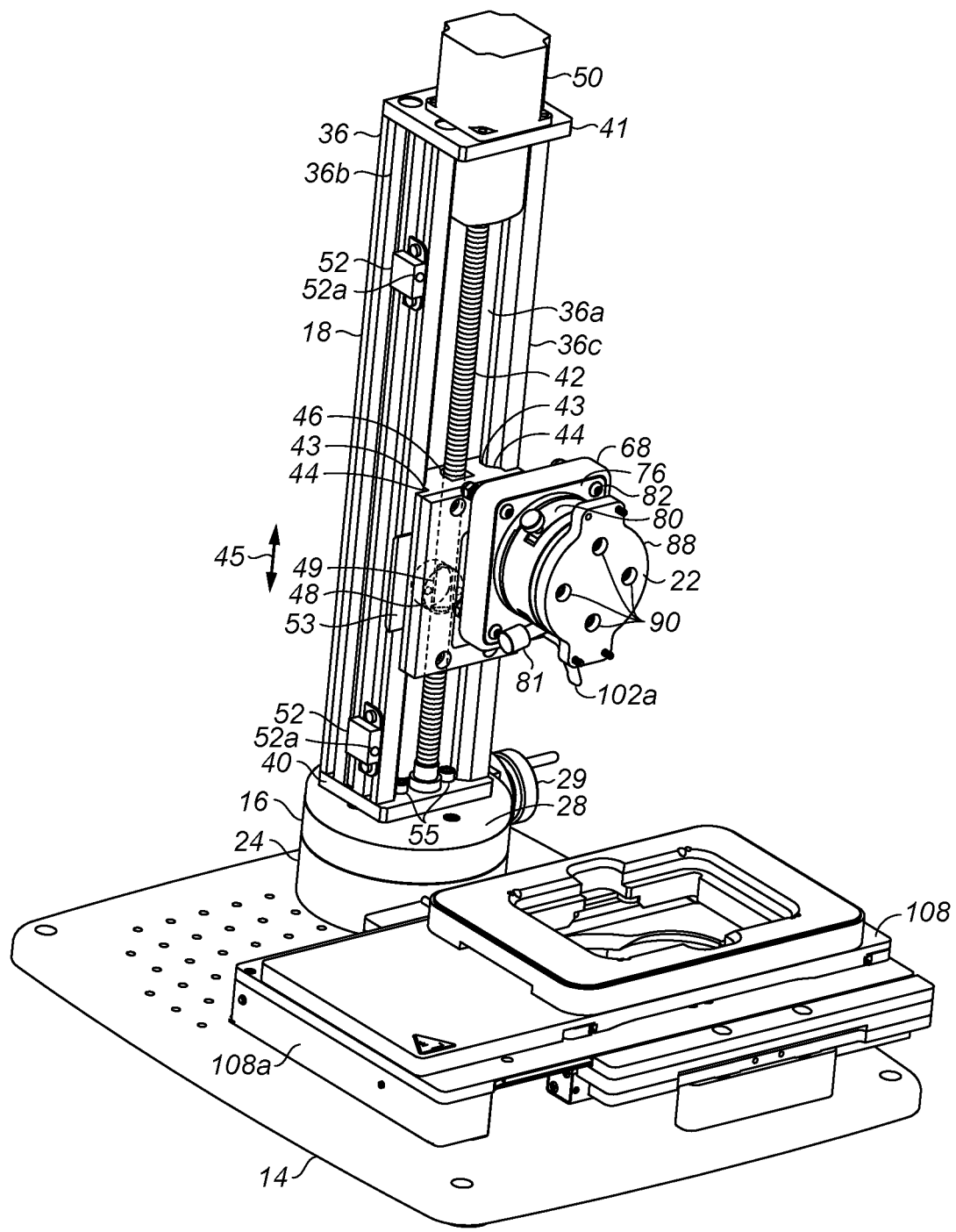
FIG. 4 is another view of FIG. 1 with the z axis stage of FIG. 3 shown mounted upon the x-y stage, and the imaging head removed.

Vertical stage 18 has a housing 36 that extends upwards from rotary stage 16 and platform 14. Carriage 20 is received along an open side 36a of housing 36 and mounted for vertical translation between sides 36b and 36c of housing 36. As best shown in FIG. 4, housing 36 has a bottom wall 40 and a top wall 41 between which is journaled are two ends of a rotatable vertical lead screw 42 that extends through a vertical opening 46 of carriage 20. Carriage 20 has two vertical slots or grooves 43 that ride along two inwardly protruding rails 44 from opposing sides 36b and 36c of housing 36. Lead screw 42 extends along a threaded hole 49 of a nut 48 (shown in dashed lines) fixed in carriage 20. The threads of lead screw 42 engage the threads of nut 48 along hole 49 so that rotation of lead screws 42 moves nut 48 and thus carriage 20 attached thereto up and down vertically along rails 44. Rotation of the lead screw 42 in a first direction causes the carriage 20 to move upwards, and in a second direction causes the carriage to move downwards, as indicated by arrow 45. A stepper motor 50 is mounted along the top of housing 36 and extends through an opening in top wall 41 to engage the top end of lead screw 42. Motor 50 control the rotation and direction of rotation of lead screw 42 and thus the vertical height of carriage 20 with respect to the horizontal dimension along which platform 14 extends. Vertical stage 18 is preferably a Velmex BiSlide® model number MN-0100-M02-21, but other vertical stages may also be used. Stepper motor 50 may be a Vexta Stepper Motor Model No. PK266-03A-P1 (manufacturer: Oriental Motor Co. Ltd., Japan), but other stepper motors may be used. To mount vertical stage 18 to turntable 28 of rotary stage 16, bottom wall 40 of housing 36 has holes 54 (FIGS. 3 and 4) through which four screws 55 extend into threaded holes 56 of the adapter plate 32, where two screws 55 are shown in FIG. 3, and the other two screws 55 are shown in FIG. 4.

Two limit switches 52 are provided each having a switch element 52a which actuates when abutted by an extension 53 from carriage 20 to define the uppermost extent and lowermost extent of carriage 20 travel up and down, respectively. When actuated, the limit switch 52 sends a signal to a below discussed controller 135 to turn off motor 50 operation to avoid over travel of carriage 20 in housing 36.

The mounting arm (or assembly) 22 coupling carriage 20 to housing 13 of imaging head 12 will now be described and is best shown by the cross-sectional view of FIG. 5, and exploded views of FIGS. 6 and 7. An adapter mount plate 58 is attached to a slanted/angled support member 60 by a screw 61 via hole 62 in plate 58 and threaded hole 63 in support member 60, where pins 64 extend from support member 60 and align with holes 65 of adapter mount plate 58. A tray member 68 is attached to support member 60 by a screw 70 via a hole 69 of tray member 68 received in a threaded hole 71 of support member 60, where pins 72 extend from support member 60 and align with holes 74 in the bottom of tray member 68.

Tray member 68 receives a tilt plate 76 which has been attached by screws 77 via holes 78 in tilt plate 76 into threaded holes 79 of a base 80a of a rotary stage 80, which has a turntable 80b rotatable with respect to base 80a. Two ball bearings 66 are disposed in tray member 68 between the inside of tray member 68 and bottom of tilt plate 76. Such ball bearings 66 are each glued in a semicircular pocket along the interior bottom of tray member 68 prior to receiving tilt plate 76 with attached rotary stage 80 in order to provide two points of contact with tilt plate 76 near the top left and top right of tray member 68. Four screws 82 extend through holes 83 in tilt plate 76 and holes 84 in tray member 68 and are each captured by one of four nuts 86 via one of four springs 85. Springs 85 and nuts 86 are also shown in FIGS. 1-3. Springs 85 bias tilt plate 76 toward the inside bottom of tray member 68 with two ball bearings 66 being disposed there between. An adapter mount plate 88 is attached by screws 89 via holes 90 in plate 88 to threaded holes 91 along turntable 80b of rotary stage 80. Screws 92 extend through holes 94 in plate 88 into threaded holes 95 (FIG. 7) along base 15 of housing 13 of imaging head 12. The mounting arm 22 is mounted by four screws 96 which extend via holes 98 of plate 58 into threaded holes 100 (FIG. 6) for receiving such screws 96 along carriage 20. The slant/angled support plate 60 is set at a desired upward angle or slope to dispose the rest of the mounting arm 22 mounted to plate 60 at a higher height than would be if support plate 60 was horizontally disposed in order to obtain a desired range of vertical travel of imaging head 12 as set by the position of switches 52 along housing 36. However, other angle or non-angled (i.e., horizontal) support member may be used depending on the desired height of vertical stage 18, and the range of vertical travel of carriage 20 as set by limit switches 52. For purposes of illustration, only one of each set of screws, springs, holes, and nuts, are labeled in FIGS. 6 and 7.

Figure 5:
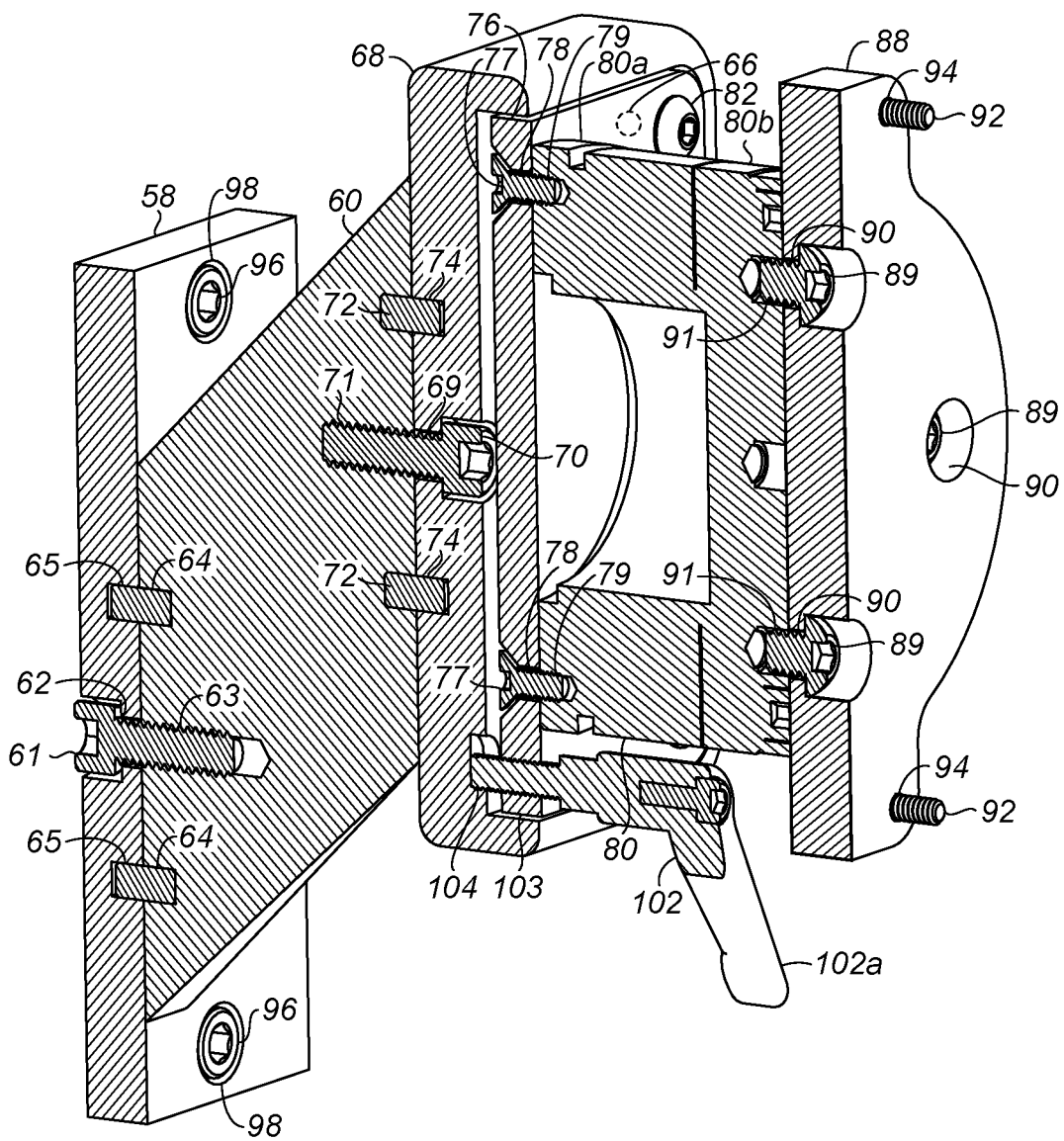
FIG. 5 is a partial cross-sectional view of FIG. 1 taken along line 5-5 in the direction of arrows at the end of the line showing the mounting arm which couples the imaging head to a carriage of the vertical stage.

As best shown in FIG. 5, a thumb screw 102 with attached handle or knob 102a is provided to adjust tilt of plate 76 with respect to tray member 68. Thumb screw 102 extends through a threaded hole 103 near the center bottom of plate 76 against an opening 104 along the inside of tray member 68 which abuts the end of thumb screw 102. The thumb screw 102 rotation changes the distance of the bottom of plate 76 with respect to the bottom of tray member 68 under the bias of springs 85, while the ball bearings 66 provide two points of contact upon which plate 76 tilts, thereby controlling the tilt or yaw (or tilt angle) of the normal axis 128b (FIGS. 1 and 2) of the housing 13 of imaging head 12 with respect to the horizontal via the attached rotary stage 80, as denoted by arrows 105 (FIG. 1). The tilt position of the imaging head 12 may thus be varied from the horizontal as desired by the user, such as for example at or between 0 to 5 degrees. Tray member 68, plate 76, adapter plates 58 and 88, and support member 60 may be made of aluminum.

Rotary stage 80 operates to rotate turntable 80*b* with respect to base 80*a* responsive to rotation of a knob or micrometer 81 to gearing (not shown) disposed to rotate turntable 80*b* as indicated by arrow 106 (FIG. 1) about the normal axis 128*b*. A locking pin 107 may slide or be turned to move in and out with respect to a hole in base 80*a* in order to lock and unlock, respectively, the rotational position of turntable 80*b* with respect to base 80*a*. Turntable 80 is rotatable 360 degrees to rotate imaging head 12 about normal axis 128*b* and may have graduations along its outer circumference in rotational degrees with respect to marking(s) along base 80*a*, which may be utilized by a user when manually turning knob 81 clockwise or counterclockwise to effect desired rotation. The rotary stage 80 is preferably a Newport Precision Rotation Stage Model No. UTR80 (manufacturer: Newport Corporation, Irvine, Calif., USA), but other rotary stages may also be used. Thus, plate 58, support member 60, and tray member 68 extend along a first portion of mounting arm 22 which is fixed to carriage 20 as described above, and tilt plate 76, rotary stage 80, and plate 88 extend along a second portion of mounting arm 22 coupled to the imaging head 12, as described above, so that the second portion tilts with respect to the first portion by tilting plate 76 in tray member 68 of the first portion to adjust tilt of the imaging head 12 along normal axis 128*b* with respect to the horizontal dimension along which surface 14*a* of platform 14 extends.

In summary, the entire mounting arm 22 with imaging head 12 can rotate with vertical stage 18 using rotary stage 16 (arrow 30) to a desired rotational position about the vertical dimension (with locking pin 27 temporarily released until new rotational position is reached) using hand crank 29. The entire mounting arm 22 with imaging head 12 can be set to a desire height or distance along the vertical dimension using vertical stage 18 (arrow 45) from the horizontal dimension along which surface 14*a* of platform 14 extends. Thumbscrew 102 of the mounting arm 22 can be turned using handle 102*a* to adjust tilt plate 76 to a desired tilt position with respect to tray member 68 (arrow 105), and imaging head 12 can rotate using rotatory stage 80 (arrow 106) to a desired rotational position about normal axis 128*b* that extend through of the imaging head 12 and along the rotational axis of rotary stage 80 about which turn table 80*b* rotates (with locking pin 107 temporarily released until new rotational position is reached). This freedom of motion along arrows 30, 45, 105, and 106 allows imaging head 12 in a first mode of operation of microscope 10 to be moved to a position, such as shown in FIG. 1 to image, for example, a first (or ex-vivo) tissue sample 110 between imaging head 12 and platform 14, and in a second mode of operation of microscope 10 moved to a position such as shown in FIG. 2 to image, for example, a second (or in-vivo) tissue sample 113 of a patient/subject beside (i.e., at the side of, nearby, but not upon) platform 14. In-vivo tissue sample 113 has, for example, a skin lesion 113*a*. The patient/subject is not shown to scale in FIG. 2.

As stated earlier, objective lens 128 extends in snout 127 from housing 13. Snout 127 may have an optional snout cover 127*a* with a material plate window 127*b* of optically transparent material, such as glass or plastic. Preferably, window 127*b* is thick, such as 1 *mm*. Cover 127*a* is shaped to extend over snout 127 and objective lens 128 with imaging being carried out through window 127*b*. It is especially useful so that pressure may be applied by the window 127*b* against a surface of tissue being imaged, such as an in-vivo tissue sample, to assist in stabilization of the optical system 11 of the imaging head 12 to such tissue to improve imaging performance. The snout cover 127*a* and window 127*b* may also be used to image in-vivo samples, such as small animals, that may be placed upon platform 14 with or without specimen stage(s) present.

In such first mode of operation, ex-vivo tissue sample 110 may be mounted onto a movable specimen stage provided by a third (or x-y) stage 108 movable along x and y orthogonal axes (depicted as x and y arrows in FIG. 1) which are parallel to the horizontal plane of surface 14*a* of platform 14 upon which stage 108 is mounted. For example, ex-vivo tissue sample 110 may a non-histologically prepared tissue specimen (i.e., without being mechanically sliced thin sections mounted on slides) removed from a patient/subject which is disposed upon a block 111. Block 111 may represent a substrate, such as of glass or plastic, or a cassette which retains the tissue sample 110 in a desired orientation on stage 108. Mounting features or inserts 109 receive block 111, and clips 112 retain block 111 position in stage 108. However, other mechanisms for retaining block 111 may be used. While stage 108 may be a typical translation stage for moving tissue sample 110 along x and y orthogonal dimensions, preferably stage 108 is a Marzhauser X-Y Stage Scan$^{Plus}$ Model No. 00-24-579-0000 (manufacturer: Märzhäuser Wetzlar GmbH & Co. KG, Germany). Stage 108 is mounted to platform 14 as typically in mounting stages to bases, such as by screws 109*a* through holes in stage 108 in stage mounts 108*a* attached to platform 14. Preferably, two stage mounts 108*a* are used as shown in FIG. 2 between stage 108 and platform 14. Stage mounts 108*a* may be attached to platform 14 by screws via holes through such mounts 108*a* and platform 14. Rubber o-rings and washers (such as tooth lock washers) may be disposed along such screws 109*a* in attaching the stage 108 and stage mounts 108*a* (FIG. 2), in which o-rings aid in minimization of vibration to block 111 holding tissue sample 110. Other mechanisms for coupling stage 108 to platform 14 may also be used. Four rubber feet 115 are attached to the underside of platform 14, such as by screws through holes in the platform, so that the platform may rest on a tabletop or other surface upon such rubber feet.

Figure 6:
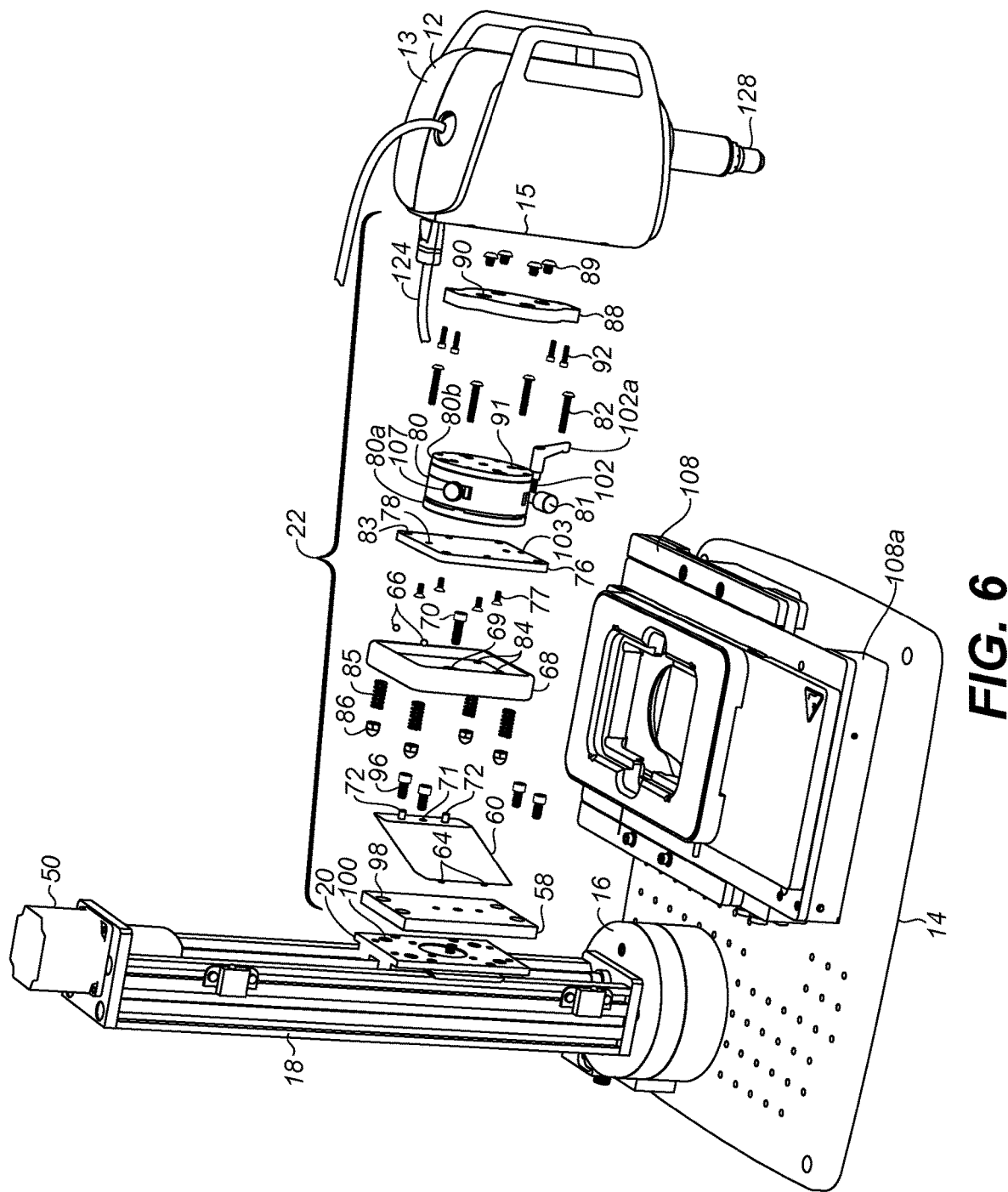
FIG. 6 is another view of FIG. 1 in which the assembly of the mounting arm of FIG. 5 is shown exploded between the imaging head and the carriage of the vertical stage, where the z-stage of FIG. 3 is mounted to the x-y stage.
Figure 7:
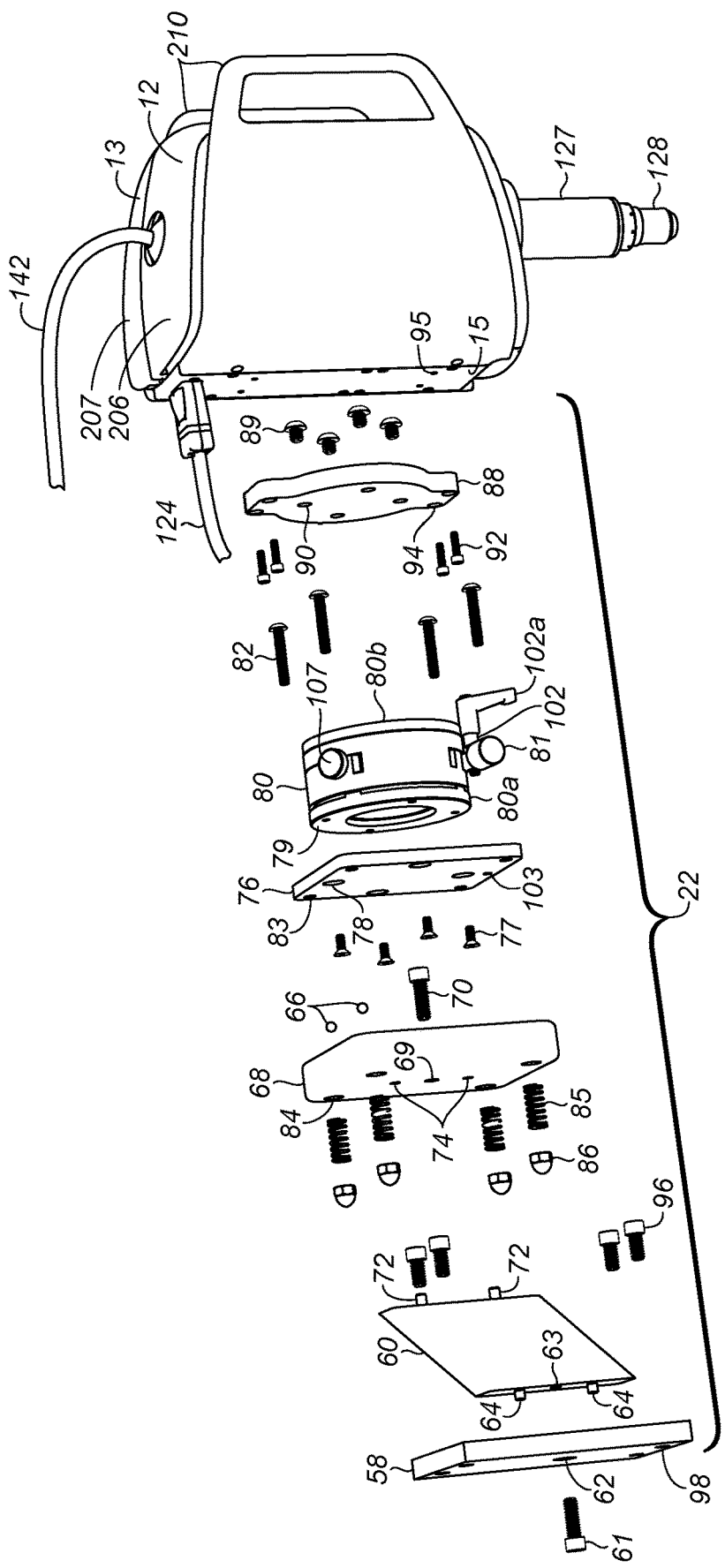
FIG. 7 is another exploded view of the assembly of the mounting arm of FIG. 5, but from a different angle of that of FIG. 6, and having the rotary stage, vertical stage, and platform removed.

Optionally, an additional fourth (or z) stage 114, such as shown in FIGS. 3, 4, and 6, may be attached atop stage 108 in which the mount for tissue sample 110 as shown in FIG. 1 is removed and placed upon stage 114 instead. Stage 114 is movable along a z axis orthogonal to the x and y axes of stage 108. Stage 114 preferably is a Marzhauser Piezo Z-Stage Model No. 00-55-550-0800, which attaches by clips onto stage 108, for coupling such stages as set forth by the manufacturer.

Figure 8:
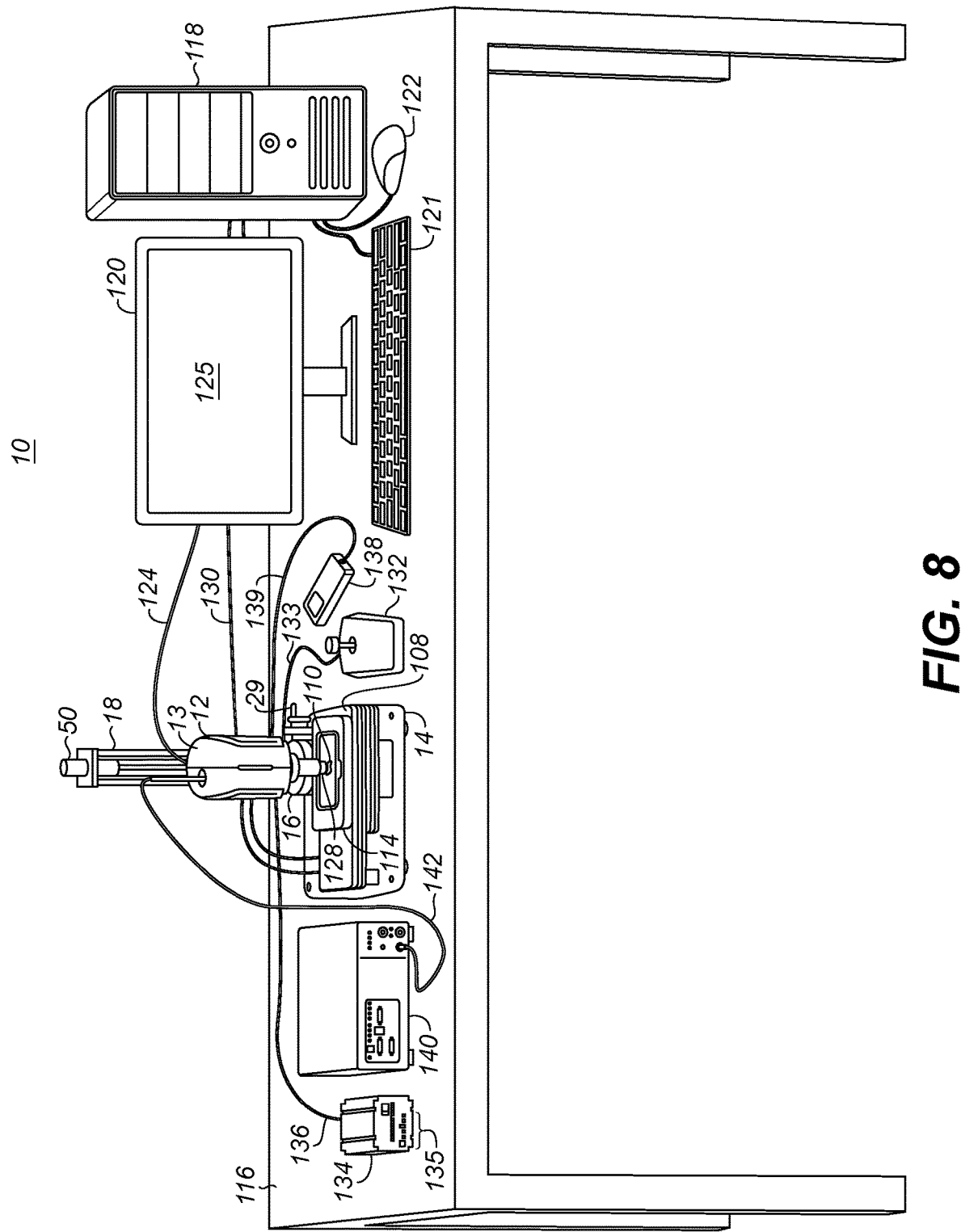
FIG. 8 is a block diagram of the microscope of the present invention having an imaging head supported over a platform as shown in FIG. 1 with a computer system, a display for showing images captured by the microscope, and a multi-wavelength laser light source which may provide additional imaging wavelengths of light, as well as other components for controlling position of the vertical stage, x-y stage, and z-stage.

Referring to FIG. 8, an example of microscope 10 in a desktop or table configuration is shown having platform 14 disposed upon a surface 116 with imaging head 12 mounted to platform 14 as described above to enable both first and second modes operation of the microscope. The microscope 10 has a computer system 118, such as a personal computer or workstation programmed in accordance with software in its memory. Computer system 118 is connected to a display 120 and user interface devices (such as keyboard 121 and mouse 122). Display 120 may be a touchscreen display which provides an additional user interface device to graphical user interface software operating on computer system 118. Computer system 118 is connected by a cable 124 to imaging head 12, and via such cable the computer system controls operation of imaging head 12 and receive signals therefrom representative of one or more microscopic images of optically formed tissue sections at one or more locations within or upon tissue sample 110 or 113 for output to display 120 and storage in memory of the computer system in the same manner as VivaScope® confocal microscopes manufactured by Caliber Imaging & Diagnostics, Inc. of Henrietta, N.Y., USA. The location of the platform 14 upon surface 116 may be different than shown in FIG. 8 so that imaging head 12 can be properly positioned with respect to a patient or subject that needs to located beside both surface 116 and platform 14 in order to image in-vivo tissue of such patient or subject in the second mode operation of microscope 10.

In microscope 10 operation, scanned laser illumination is focused and collected by objective lens 128 along its optical axis 128a into tissue sample 110 or 113, where collected light by the lens is representative of a tissue section at a cellular level below the surface of the tissue sample facing objective lens 128. While FIG. 8 shows an example of first mode operation for imaging an ex-vivo tissue sample of FIG. 1, the housing 13 is movable for imaging an in-vivo tissue sample as described earlier for second mode operation of microscope 10 as shown in FIG. 2. As stated earlier, tissue samples may also be positioned on platform 14 for imaging by imaging head 12 without stage(s) 108 or 114 present, such as may be useful for imaging in-vivo tissue samples of small animals.

The electronics of imaging head 12, and the computer system 118 of microscope 10 with display 120, for viewing microscopic sectional images of tissue samples from light focused and collected via objective lens 128, may be the same as described in incorporated by reference U.S. Pat. No. 9,055,867. While in FIG. 8 both stages 108 and 114 are shown when imaging ex-vivo tissue samples, z-stage 114 is optional, since objective lens 128 is movable in housing 13 along its optical axis 128a which can be aligned with a z axis orthogonal with the x and y axes of stage 108 so that objective lens 128 is thus movable along such z axis in order to select the depth of focus of a beam scanned at locations upon or within the tissue sample being imaged. However, when z-stage 114 is present upon platform 14, z-stage 114 may also be used to select the depth of focus a beam scanned at locations upon or within the tissue sample being imaged. Imaging head 12 is temporarily fixed in position with respect with respect to the x and y axes of x-y stage 108 in the first mode of operating microscope 10.

Computer system 118 controls movement of x, y motors of the stage 108 and reading x and y positions thereof, and z axis motor and reading z portion thereof of stage 114 (if present), via one or more cables 130 to ports 129. FIG. 3 shows ports 129 with cable 130 removed. Preferably a stage controller card is provided in the computer system 118 to enable such interface with stages 108 (and 114 if present) via cable(s) 130. In the case of Marzhauser_X-Y Stage and Marzhauser Z-Stage as described earlier are utilized, such stage control card may be a Scan$^{Plus}$ Marzhauser X&Y Stage Controller Card, Part Number 00-76-150-0813, located inside the case of computer system 118. An optional joystick 132, may also be used by a user to control movement of x, y axis motors of the stage 108 (and z axis motor of stage 114 if present), via a cable 133 to one of ports 130.

The stepper motor 50 of vertical stage 18 is controlled by a motor controller 134 which drives motor 50 via signals along a cable 136 to rotate lead screw 42 of the vertical stage 18 in first and second directions that enable up and down motion, respectively, of carriage 20 and the imaging head 12 mounted thereto by mounting arm 22. Limit switches 52 are also connected to motor controller 134 via cable 136 to receive signals therefrom and control motor 50 accordingly as described earlier. Buttons and switches 135 along the motor controller 134 are provided to control motor operation. Preferably, motor controller 134 is a Velmex Stage Controller Model No. VXM-1. An optional joystick 138 may connected by cable 139 to motor controller 134 to facilitate user control of motor 50 to provide desired up and down motion of carriage 20 of vertical stage 18. Preferably, joystick 138 is a Velmex Digital Joystick Model No. 4-2121. While rotary stage 16 is shown as being manually controlled by knob 29, optionally stage 16 may have a motor instead of knob 29 for rotating rotary stage 16, such as manufactured by Velmex. This optional motor may be controlled by signals from motor controller 134 which can additional drive such motor. Although not shown, power is supplied to various components in FIG. 8 to enable their operation.

In operating microscope 10 using stage 108, the optical axis 128a of objective lens 128 is aligned along a z axis perpendicular to the x and y axes of stage 108, such as shown in FIG. 1. This further enables alignment along the z axis of stage 114 if present. Such alignment is enabled by adjusting the tilt of imaging head 12 using handle 102a of thumb screw 102 and rotation of imaging head 12 using rotary table 80, as described earlier. Such may be aided by alignment mark(s) if present along rotary table 80 along turntable 80b and base 80a. Further, a target or features may be placed on the platform 14, or stage mount (in place of block 111 of FIG. 1), in view of objective lens 128 to assist in electronic calibration of images on screen 125 of display 120 as such calibration alignment is carried out to assure horizontal levelling of imaging head's normal axis 128b with respect to platform 14, where such normal axis 128b lies perpendicular to the z axis.

While the operation and structure of imaging head 12 may be the same as described in incorporated U.S. Pat. No. 9,055,867 using the laser illumination source provided therein (such as light source 146 of FIG. 9), the imaging head of the incorporated patent preferably is adapted to that of optical system 11 (FIGS. 9-11) which utilizes multiple discrete laser wavelengths for illumination provided from a multiple wavelength laser light source 140 via a fiber optic cable 142 to imaging head 12. For example, light source 140 may be a Toptica iChrome MLE-L Multi-Laser Engine (manufacturer: Toptica Photonics AG, Germany) with collimated laser diode assemblies manufactured by Blue Sky Research of Milpitas, Calif. USA. The additional laser illumination provided by light source 140 is combined with the laser illumination produced in imaging head 12 and scanned together via objective lens 128, and then returned scanned illumination via objective lens 128 is split for detection onto two detectors that sense particular wavelength(s), as described in more detail below in connection with FIGS. 9, 10, and 11.

Referring to the optical system 11 of FIG. 11, linear polarized light of multiple discrete wavelengths generated by light source 140 (e.g., 405 nm, 488 nm, 561 nm, and 640 nm) passes along optical fiber cable 142 to optics 143 which collimates and expands its size to provide a beam 144, such as to 4.3 mm in diameter. Optics 143 are preferably contained in a cylindrical tube 143a that receives optical fiber cable 142 and extends through an opening 13a (FIG. 1) of housing 13. A laser 146, preferably a laser diode which is associated with an opto-detector for monitoring laser power as described in the incorporated patent, provides a linearly polarized beam 148 at a single wavelength (e.g., 785 nm). Beam 144 and beam 148 are combined into a beam 150 by a dichroic beamsplitter 149, and beam 150 then passes through a polarizing beamsplitter 150. A resonant scanner 152 presents its scanning mirror 152a to beam 150, and the beam from the resonant scanner mirror 152a is then incident scanning mirror 154a of a galvanometer 154 to provide a scan beam 155. Mirrors 152a and 154a oscillate so that mirror 152a provides fast or horizontal line scans in a raster being scanned, and slow or vertical scan and retrace are provided by mirror 154a, as described in more detail in the incorporated patent. The axes of oscillation of these mirrors 152a and 154a are orthogonal (perpendicular) to each other. The separation distance may be approximately a minimum separation distance to provide clearance between the mirrors 152a and 154a as they scan. A telescope 156 magnifies the beam (e.g., 2.3×) and relays scanning beam 155 to objective lens 128 via a quarter wave plate shifter 157, and the objective lens 128 focuses the scanning beam 155 to the sample, such as sample 110 or 113 for example as earlier described.

The returned light 158 from the tissue sample 110 or 113 passes through objective 128, wave plate 157, telescope 156, and scanning mirrors 154a and 152a. The return light thus is descanned at mirrors 154a and 152a into a stationary beam 160 and enters the polarizing beamsplitter 151 which reflects beam 160 via a focusing lens 161, a reflecting mirror 162, and a notch filter 163, to a dichroic beamsplitter 164 which splits the returned light into a first beam 165 and a second beam 169. Beam 165 is incident a small aperture provided by pinhole 166 onto a detector 168 provided by a photomultiplier tube, via one of selectable open or filter positions along a filter wheel 167. Beam 165 is incident a small aperture provided by a pinhole 170 onto a detector 172 provided by a photomultiplier tube, via one of selectable open or filter positions along a filter wheel 171. Lens 161 focuses the light of their respective beams onto pinholes 161 and 170. Although not shown in FIG. 11, a turning mirror 173 (FIG. 9) is provided between beamsplitter 151 and mirror 152a to reflect beam 150 onto mirror 152a, and reflect beam 160 from mirror 152a to beamsplitter 151. By virtue of mirror 162 being in the detection path after return light 158 is descanned by oscillating mirrors 152a and 154a, mirror 162 is thus not involved in scanning and thus may be referred to as a non-scanning mirror.

Each of filter wheels 167 and 171 has a shaft mounted for rotation by stepper motors 174 and 175, respectively, to select the desire opening or filter along the wheel. For example, at least four filters are provided along wheel 167 for different wavelength(s) or range of wavelengths onto detector 168, where filter 167a passes light only in range of 405-561 nm wavelength, filter 167b passes only 630 nm wavelength light, filter 167c passes only 670 nm wavelength light, and filter 167d passes both 832 nm and 837 nm wavelength light. At least two filters are provided along wheel 171, where a filter 171a passes only 520 nm wavelength light, and a filter 171b passes only 450 nm wavelength light. Spaces on one or both filter wheels are open so that unfiltered light may pass there through, such as for detection of light of the wavelength of laser 146 in the path of light for detection by their respective detectors 168 and 172. For example, opening 167e is provided on filter wheel 167, and opening 171c is provided on filter wheel 171. Additional openings/filters illustrated on filter wheel 171 may have filters for other wavelengths or wavelength ranges.

The wavelengths provided along fiber optic cable 142 can activate fluorescent dyes that may be applied to tissue samples. Thus, one of the filter wheels enables selection of a filter to detect on their associated detector the fluorescent wavelength(s) of the returned light 160, while the other of the filter wheels is set to an open position to detect light of wavelength of laser 146 in the returned light 60. Notch filter 163 allows selectable discrete wavelengths or ranges of wavelengths to assist in detecting wavelengths with filters along the filter wheels. Preferably, notch filter 163 allows light of wavelength of laser 146 (e.g. 785 nm), and blocks light of wavelengths received from fiber optic cable 143 which may interfere with imaging at fluorescent wavelengths associated with the filters disposed along filter wheels 167 and 171 in the path of light for detection by their respective detectors 168 and 172. Further, dichroic beamsplitter 164 may filter light such that beam 165 has wavelengths 405 nm and 408 nm, and a beam 169 has wavelengths 581 nm, 640 nm, and 785 nm. Other wavelengths than set forth above may be used for light sources 140 and 146, and detected beams 165 and 169, as well as other wavelength filtering may be used by notch filter 163 and along filter wheels 167 and 171.

Each motor 174 and 175 is driven by electronics on a printed circuit board 185 having a Hall effect sensor which reads a magnet along the wheel to sense the home position of the wheel and rotate the wheel to the desired filter or open location along the wheel by actuation signals received from computer system 118. The rotational position of each filter or opening along filter wheels 167 and 171 may be stored memory of the computer system 118 so that motors 174 and 175 can be actuated by computer system to arrive at the rotational position associated with the desired filter or opening along the wheels.

The optical components and electronics of the imaging head 12 are mounted along a chassis 176 and support plate 177 as shown in FIGS. 9 and 10 to provide a preferred compact mounting of such components. Two printed circuit boards 190 with electronics for controlling imaging head 12, responsive to computer system 118, are attached to chassis 176, where circuit board 190 are connected to other circuit boards described herein in housing 13. A first structure or block 178, such as of aluminum, is mounted to chassis 176 which supports light source 146, beamsplitter 149, and cylinder 143a with attached fiber optic cable 142. Structure 178 has a receptacle 179 into which cylinder 143a plugs into when additional wavelengths for imaging from fiber optic cable 142 is desired. Detectors 167 and 172 have a circuit board 182 and 183, respectively, which is mounted to support plate 177. A second structure or block 180, which may also be of aluminum, is mounted to chassis 176 to support filter wheels 167 and 171, pinholes 167 and 170, beamsplitter 164, and notch filter 163, for imaging onto such detectors 167 and 172 as described earlier. The circuit board 185 for driving and controlling motors 174 and 175 may be supported on circuit board 182.

In order to properly align beams 165 and 169 for detection, mirror 162 and pinhole 166 are each adjustable in position. Mirror 162 is mounted upon an adjustable flexure 162a attached to a bracket or flange 186 of chassis 176 for steering beam 169 via beamsplitter 164. Flexure 162a may be adjustable by screws, and for example may be a stainless steel flexure mirror mount, such as Flexure Industrial Optical Mount with Allen (or hex) key adjustments, model No. MFM-050 manufactured by Newport Corporation of Irvine, Calif., U.S.A. This adjustability of mirror 162 spatial position is denoted by arrows beside mirror 162 in FIG. 11. Pinhole 166 (i.e., provided by a thin substrate with light blocking material having a small aperture) is retained in a cylinder (or cylindrical cell) 188 mounted in structure 180, where pinhole 166 is spring loaded using two spring steel flexures. Two orthogonally oriented set screws 189 push pinhole 166 into a desired position against the spring force of such flexures, so that turning screws 189 adjusts pinhole 166 position. Optionally, such adjustability may be similar provided in structure 180 in a third orthogonal dimension. This adjustability of pinhole 166 spatial position in two dimensions orthogonal to the incident beam 165, or in three dimensions, is denoted by arrows beside pinhole 166 in FIG. 11.

When imaging head 12 is assembled, mirror 162 is adjusted in position to steer beam 169 in alignment with pinhole 170, which is fixed in position, so that beam 169 detected by detector 172 can be properly imaged. To aid in such alignment, an image is displayed on display 120 by computer system 118 from detector 172, and adjustable mirror 162 is moved until beam 169 is aligned with the fixed pinhole 170 such that highest signal level from detector 172 is achieved on display 120. Then an image from detector 168 is displayed on display 120, and adjustable pinhole 166 is moved until the highest signal from detector 168 is achieved on display 120. Thus, beam 165 is now aligned with pinhole 166 so that beam 165 detected by detector 168 can be properly imaged. Alternatively, adjustable flexure 162a is not used so that mirror 162 is mounted non-adjustable in position when imaging head 12 is assembled, and pinhole 170 is manually adjustable in position in the same way pinhole 166 is disposed. In such case, one or preferably both pinholes 166 and 170 are each separately adjusted in position to align their respective beams 165 and 169 onto their respective detectors 168 and 172 by the highest signal being achieved on display 120 from their respective detectors 168 and 172.

The adjustability in alignment of beams 165 and 169 assures proper operation of dual detection path of optical system 11 of the beams onto detectors 168 and 172, respectively, so that microscope 10 can simultaneously provide images of microscopic structures of the same tissue sample using two different wavelengths or wavelength range of detected returned light from the sample. Filter wheels 167 and 171 are each set to one of openings or filters accordingly, so that one or both images of the desired wavelengths or wavelength range can appear on display 120 by computer system 118 from received signals of detectors 168 and 172. Pinholes 166 and 170 may be identical, and they enable confocal imaging on their respective detectors by limiting returned scattered light of their respective beams to a particular section within or on the tissue sample 110 or 113.

Attached to the forward end of chassis 176 is a fixed tube 192 with optics providing telescope 156. Objective lens 128 is disposed in a generally cylindrical mounting 194 that attaches to a barrel 196 providing a tube or sleeve moving axially (along optical axis 128a) over tube 192 by a linear actuator as described in the incorporated patent. A magnetic strip is provided on the side of barrel 196 which is read by a sensor 197 on chassis 176 that linearly encodes position of the barrel 196 to the electronics in the imaging head 12, thereby enabling computer system 118 to actuate the linear motor to adjust the position of objective lens 128 with respect to telescope 192 and hence the focus of such lens with respect to the tissue sample 110 or 113.

Preferably, cylindrical magnets 198 are attached, such as by adhesive, to holes 199 along the interior annular ring 200 at end of barrel 196, as shown in FIG. 9. A metal ring 201 is attached to the objective lens mounting 194. Such ring 201 attaches along ring 200 by magnetic attraction to magnets 198, so that mounting 194 is retained to barrel 196. The objective lens 128 shown in the figures represents a liquid immersion lens. Such objective lens 128 is useful when a refractive index matching fluid is applied to a tissue sample prior to being imaged (the fluid matches or approximately matches the refractive index of the tissue sample) as the objective lens is brought into contact with the surface of the tissue sample. The index matching fluid reduces undesirable reflections and spherical distortions from the tissue sample's surface facing the lens that can negatively effect imaging performance. However, different objective lens may be provided in different mountings 194, each providing a different imaging performance, such as in terms of magnification, or are of non-immersion or different immersion type lenses. When a different objective lens 128 is desired by a user, the user can pull mounting 194 away for magnetics 198, and replace with a different mounting 194 with the desired objective lens. Alternatively, the mounting 194 may be attached such as by adhesive, to the end of barrel 196, without metal ring 201 or magnetics 198.

The earlier described snout 127 is provided by barrel 196 with attached mounting 194 having objective lens 128. As shown in FIG. 9, snout cover 127a is provided by a cylindrical tube having a window 127b mounted in a cap 127c that is received in an opening 127e at the distal end of such tube which is shaped to receive cap 127c. To mount snout cover 127a to imaging head 12, a cylindrical mounting 202 is provided having three legs 203 that attach, such as by adhesive, to the front of chassis 176 and extend via an opening 13b at the front of housing 13 with barrel 196. Along the front inner annular rim 204 of mounting 202 are holes 204a for cylindrical magnets 205 which are retained in the holes by adhesive. A metal ring 127d is attached at the rear of the tube providing snout cover 127a. Attraction of ring 127d to magnets 205 along rim 204 retains snout cover 127a in position for imaging through window 127b via objective lens 128. Snout cover 127a may be removed from its mounting 202 by pulling cover 127a away from magnetics 205 when snout cover 127a is not needed for imaging.

Housing 13 has a series of ribs 208 extending from base 15 of housing 13 onto which chassis 176 and plate 177 are mounted, such as by screws into holes along such ribs. Left and right housing portions 206 and 207 provide shells that mate with each other and attach to ribs 208 by screws. Two handles 210 are then attached to housing portions 206 and 207 to assist in manually moving housing 13 by a user if desired with respect to platform 14. If a fan is provided in housing 13, a fan cover 211 may be used. Other manner of coupling imaging head 12 components within housing 13 may be used than shown in FIGS. 9 and 10.

Computer system 118 via cable 124 has an I/O interface with electronics in the imaging head 12 to enable their operation, such as to control of operation of resonant scanner 152 and galvanometer 154, control the linear actuator or motor for positioning objective lens 128 along its optical axis 128a, and power to light source 146, as may be described in more detail in the incorporated patent. The signals from detectors 168 and 172 are received along separate channels via cable 124 as raster images in memory of computer system 118 for display on screen 125 as desired by the user. Computer system 118 via cable 124 also sends signals to motor 174 and 175 and reads sensors associated therewith to rotate filter wheels 167 and 171, respectively, in accordance with the rotational position of the particular filter or opening along such filter wheels as desired by the user.

Different locations along tissue samples 110 or 113 are selected to provide optical sectioned microscopic images of the sample at such locations presented to objective lens 128 by one or more of moving imaging head 12 as described earlier, moving stage 108 along its x and/or y axes, changing depth of the scanned beam 115 in and under the surface of the tissue sample by moving objective lens 128 along its optical axis 128*a* in imaging head 12, such optical axis being co-axial with the z axis if aligned thereto as described earlier, or along z axis to change such depth by using stage 114 if present. The selection of different locations along a tissue sample 110 or 113 may be performed automatically by computer system 118 stepwise movement along x and/or y axes of stage 108 (and z axis of stage 114 if present), and/or stepwise movement of objective lens 128 along its optical axis 128*a*. For example, computer system 118 can fix the position of galvanometer mirror 154*a* to be stationary, and instead move stage 108 in a stepwise fashion along the y axis to provide comparable raster scan imaging. Power and ground to electronics and other components, such as laser source 146, in imaging system 12 is also provided by wires within cable 124.

Further, although imaging head 12 is described herein having an optical system for capturing optically formed microscopic sectional images of tissue sample 110 or 113 operative by confocal microscopy, other modalities for imaging optically sectioned microscopic images of sample may be incorporated in imaging head 12 by optical coherence tomography (OCT) or interferometry, such as described in Schmitt et al., "Optical characterization of disease tissues using low-coherence interferometry," Proc. of SPIE, Volume 1889 (1993), or by a two-photon laser microscopy, such as described in U.S. Pat. No. 5,034,613.

Other positions of imaging head 12 may be provided than shown in the figures. Also, different non-histologically tissue samples than tissue samples 110 and 113 shown in the figures may be imaged by microscope 10.

From the foregoing description, it will be apparent that a confocal microscope having a positionable imaging head has been provided. Variations and modifications in the herein described microscope, and system and method for mounting an imaging head of such microscope in accordance with the invention, will undoubtedly suggest themselves to those skilled in the art. Accordingly, the foregoing description should be taken as illustrative and not in a limiting sense.

The invention claimed is:

1. A microscope for imaging tissue comprising:
   an imaging head having an optical system for capturing optically formed microscopic sectional images;
   a platform upon which is disposed a first stage coupled to a second stage, wherein said second stage is mounted upon said platform, said first stage is coupled to said imaging head for moving said imaging head along a vertical dimension perpendicular to a horizontal dimension along which said platform extends, and said second stage rotates said imaging head and said first stage about said vertical dimension, wherein said imaging head is positionable using at least said first stage and said second stage in a first mode to image at least a first tissue sample disposed between said imaging head and said platform, and in a second mode to image at least a second tissue sample disposed beside said platform; and
   a specimen stage mountable to said platform for supporting said first tissue sample in said first mode, in which said specimen stage is movable at least along x and y orthogonal axes along said horizontal dimension.

2. The microscope according to claim 1 wherein said imaging head is moved between said first mode and said second mode by at least rotation of said second stage.

3. The microscope according to claim 1 wherein said second stage is mounted to said platform, and said second stage is a rotary stage mounted to said first stage for rotating said first stage and said imaging head 360 degrees about said vertical dimension, and said first stage is a vertically disposed motor driven linear slide stage.

4. The microscope according to claim 1 wherein said first tissue sample is one of an ex-vivo tissue specimen mounted on said specimen stage or an in-vivo tissue of a subject positioned between said imaging head and said platform, and said second tissue sample is in-vivo tissue of human or animal disposed beside, not upon, said platform.

5. The microscope according to claim 1 wherein said optical system comprises at least an objective lens for focusing and collecting illumination from said first tissue sample in said first mode and said second tissue sample in said second mode, and said objective lens has an optical axis.

6. The microscope according to claim 5 wherein said specimen stage represents a third stage mounted to said platform, said first tissue sample being mounted upon said third stage in order to move said first tissue sample with respect to said objective lens in said first mode, said optical axis of said objective lens extends along a z axis perpendicular to said x and y axes, and said imaging head is temporarily fixable in position with respect to said x and y axes of said third stage.

7. The microscope according to claim 6 further comprising a fourth stage mounted to said third stage moveable along said z axis to enable said first tissue sample to be movable using said third and fourth stages along said x, y, and z axes with respect to said objective lens.

8. The microscope according to claim 5 wherein said first stage has a carriage; movable along the vertical dimension, said carriage being coupled to said imaging head by a mounting arm having a first portion fixed to said carriage, and a second portion comprising a rotary stage for rotating said imaging head about a normal axis which is perpendicular to said optical axis of said objective lens, and said imaging head is further positionable using said rotary stage of said mounting arm in said first and second modes.

9. The microscope according to claim 8 wherein said second portion is tiltable with respect to said first portion to adjust tilt of said imaging head along said normal axis with respect to the horizontal dimension, and said imaging head is further positionable by tilting said imaging head in said first and second modes.

10. The microscope according to claim 5 wherein said objective lens is movable within said imaging head along said optical axis.

11. The microscope according to claim 5 wherein said objective lens represents one of a plurality of objective lenses removably mounted to said imaging head.

12. The microscope according to claim 5 wherein said illumination is of one laser wavelength or multiple discrete laser wavelengths.

13. The microscope according to claim 1 wherein said optical system comprises at least an objective lens for focusing scanned illumination along a first path to said first tissue sample in said first mode and said second tissue sample in said second mode, and collecting returned illumination along a second path, said second path having at least a beam splitter that splits said returned illumination into a first beam and a second beam, said first beam travels to a first detector via a first pinhole and a first selected position of a first filter wheel having one of plurality of different filters or an opening, and said second beam travels to a second detector via a second pinhole and a second selected position of a second filter wheel having one of plurality of different filters or an opening, wherein said illumination along said first path is of multiple discrete wavelengths, and said first and second detectors each receive different wavelengths or range of wavelengths of said collected illumination to enable simultaneous capture of a same one of said images at said different wavelengths or range of wavelengths on said first and second detectors in accordance with said first selected position of said first filter wheel and said second selected position of said second filter wheel, wherein one or both said first pinhole and said second pinhole are separately adjustable in position to align said first beam and said second beam, respectively, onto said first detector and said second detector, respectively.

14. The microscope according to claim 13 wherein said optical system further comprises a mirror in the second path to reflect onto said beam splitter, said mirror being adjustable in position to align the first beam when split by said beam splitter onto said first detector via said first pinhole, and said second pinhole being adjustable in position to align the second beam via said second pinhole onto said second detector.

15. The microscope according to claim 1 further comprising a computer system connected to said imaging head to receive signals representative of said images, wherein said computer system shows on a display said images captured by the microscope.

16. The microscope according to claim 15 wherein said computer system controls motors to move said specimen stage at least along said x and y axes.

17. The microscope according to claim 1 wherein said optical system is operative by confocal microscopy.

18. A microscope comprising:
a platform extending along a horizontal dimension;
a linear stage for translating a carriage along a vertical dimension;
a first rotary stage mounted to said platform for rotating said linear stage about said vertical dimension;
one or more stages upon said platform movable at least along x and y orthogonal dimensions, wherein at least one of said one or more stages is mounted to said platform;
a housing having an optical system for imaging optically formed microscopic sectional images, said optical system comprising at least an objective lens for focusing and collecting illumination, and said objective lens has an optical axis; and
a mounting arm having a first portion fixed to said carriage, and a second portion comprising a second rotary stage for rotating said housing about a normal axis which is perpendicular to said optical axis of said objective lens, said second portion being tiltable with respect to said first portion to adjust tilt of said housing along said normal axis with respect to the horizontal dimension; and
said microscope has a first mode and a second mode of operation, and in said first mode said optical axis of said objective lens extends along a z axis orthogonal to said x and y dimensions to present for imaging via said objective lens a first sample upon said one or more stages upon said platform, and in said second mode of operation said housing is positioned using at least said first rotary stage to present for imaging via said objective lens a second sample disposed beside said platform.

19. The microscope according to claim 18 wherein said linear stage translates said carriage solely along the vertical dimension.

20. A microscope comprising an optical system having at least an objective lens for focusing scanned illumination along a first path to a tissue sample and collecting returned illumination along a second path, said second path having at least a beam splitter that splits the returned illumination into a first beam and a second beam, said first beam travels to a first detector via a first pinhole and a first selected position of an optical filter or opening, and said second beam travels to a second detector via a second pinhole and a second selected position of another optical filter or an opening, wherein said illumination of said tissue sample is of multiple discrete wavelengths, and said first and second detectors receive different wavelengths of said collected illumination to enable simultaneous capture of a same one of said images at said different wavelengths on said first and second detectors in accordance with said first selected position and said second selected position having at least one of said optical filter and said another optical filter, wherein one or more of said first pinhole and said second pinhole are separately adjustable in position to align said first beam and said second beam, respectively, onto said first detector and said second detector, respectively, wherein said optical system further comprises a non-scanning mirror in said second path to reflect onto said beam splitter, and said non-scanning mirror is adjustable in position, and wherein said mirror is adjustable in position to align the first beam when split by said beam splitter onto said first detector via said first pinhole, which is non-adjustable in position, and said second pinhole being adjustable in position to align the second beam via said second pinhole onto said second detector.

* * * * *